US012778398B2

(12) United States Patent
Yoshinaga et al.

(10) Patent No.: US 12,778,398 B2
(45) Date of Patent: Nov. 3, 2026

(54) INSERTION DEVICE

(71) Applicant: OLYMPUS CORPORATION, Tokyo (JP)

(72) Inventors: Takuto Yoshinaga, Hachioji (JP); Tsukasa Ota, Hachioji (JP); Xiongwei Wang, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1284 days.

(21) Appl. No.: 17/373,938

(22) Filed: Jul. 13, 2021

(65) Prior Publication Data

US 2021/0338065 A1 Nov. 4, 2021

Related U.S. Application Data

(63) Continuation of application No. PCT/JP2019/001104, filed on Jan. 16, 2019.

(51) Int. Cl.
*A61B 1/018* (2006.01)

(52) U.S. Cl.
CPC .................................... *A61B 1/018* (2013.01)

(58) Field of Classification Search
CPC ....... A61B 1/018; A61B 1/0125; A61B 1/053; A61B 1/00066; A61B 1/0051
See application file for complete search history.

(56) References Cited

FOREIGN PATENT DOCUMENTS

| | | | | |
|---|---|---|---|---|
| EP | 3266487 A1 | | 1/2018 |
| JP | H8-238215 A | | 9/1996 |
| JP | H08238215 A | * | 9/1996 |
| JP | H11-047083 A | | 2/1999 |
| JP | 2001-340287 A | | 12/2001 |
| JP | 2002095633 A | * | 4/2002 |
| JP | 2004-249008 A | | 9/2004 |
| JP | 2004249007 A | * | 9/2004 |
| JP | 2007-151595 A | | 6/2007 |
| JP | 4242172 B2 | | 3/2009 |
| JP | 2009189636 A | * | 8/2009 |

(Continued)

OTHER PUBLICATIONS

International Search Report dated Mar. 26, 2019 issued in PCT/JP2019/001104.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An insertion device includes: a tube having a first hole extending along a longitudinal axis of an insertion portion inserted into a subject and a second hole communicating with the first hole; and a frame member covering a periphery of an opening of the second hole formed on an outer peripheral surface of the tube, wherein the frame member includes a forceps channel which includes a first conduit including a first tubular path forming a first angle being an acute angle to the longitudinal axis, a second conduit including a second tubular path forming a second angle smaller than the first angle to the longitudinal axis, and an intermediate conduit including an intermediate tubular path, and the forceps channel includes a plurality of bent regions, and curvature centers of the plurality of bent regions are disposed in different directions with respect to the forceps channel.

22 Claims, 8 Drawing Sheets

(56) References Cited

FOREIGN PATENT DOCUMENTS

| | | | | |
|---|---|---|---|---|
| JP | 2011177355 | A | * | 9/2011 |
| JP | 2013-22245 | A | | 2/2013 |
| WO | 2016/143556 | A1 | | 9/2016 |
| WO | 2019/123815 | A1 | | 6/2019 |

* cited by examiner

INSERTION DEVICE

CROSS REFERENCE TO RELATED APPLICATION

This application is a continuation application of PCT/JP2019/001104 filed on Jan. 16, 2019, the entire contents of which are incorporated herein by this reference.

BACKGROUND OF THE INVENTION

1. Field of the Invention

The present invention relates to an insertion device which includes a tube having a hole along a longitudinal axis of an insertion portion to be inserted into a subject.

2. Description of the Related Art

In recent years, insertion devices, for example, endoscopes, have been widely used in a medical field and the like. Endoscopes allow observation of an organ in a body cavity by inserting an elongated insertion portion into the body cavity, which is the subject, or allow detailed observation or treatments by using a treatment instrument or a known baby endoscope which is inserted into a channel.

Note that an insertion object which is to be inserted into a channel, such as a treatment instrument or a baby endoscope, will be referred to hereinafter as a "treatment instrument".

For a channel, there is a known tube which is provided to an insertion portion and an operation portion, and which has an elongated hole (hereinafter referred to as "first hole") through which a treatment instrument is inserted.

The first hole of tube extends along a longitudinal axis of the insertion portion (hereinafter referred to as "longitudinal axis"). A distal end of the first hole along the longitudinal axis (hereinafter referred to as "distal end") has an opening serving as a treatment instrument protrusion port on a distal end surface of the insertion portion. Further, a forceps channel communicating with the first hole is branched in a direction intersecting with the longitudinal axis (hereinafter referred to as "intersecting direction") from a portion of the tube which is positioned in the operation portion. The forceps channel has an opening serving as a treatment instrument insertion port provided to the operation portion.

Therefore, in such a tube, when a treatment instrument is inserted from the treatment instrument insertion port, the treatment instrument is inserted into the first hole of the tube via the forceps channel of the operation portion, and is then caused to protrude from the treatment instrument protrusion port disposed at a distal end of the insertion portion.

To reduce a diameter of the insertion portion, in an endoscope where an insertion portion is formed of a multi-lumen tube having a plurality of holes along the longitudinal axis, one of the plurality of holes is used as the first hole.

In a case where the multi-lumen tube is used, a second hole communicating with the first hole is formed, so that an opening is formed on an outer peripheral surface of the multi-lumen tube, and a forceps channel is provided to a frame member such that the forceps channel communicates with the opening, the frame member being formed to cover the opening.

Japanese Patent Application Laid-Open Publication No. 11-47083 discloses a configuration of an endoscope where forceps channels having different intersection angles with respect to a longitudinal axis are formed in two members coupled in an intersecting direction.

In the endoscope disclosed in Japanese Patent Application Laid-Open Publication No. 11-47083, an intersection angle of a first forceps channel of a first member connected to a first hole is set to be smaller than an intersection angle in a conventional technique. Further, an angle of a second forceps channel in a second member with respect to the longitudinal axis is set to be larger than the intersection angle of the first forceps channel, the second member being connected to the first forceps channel, and having a treatment instrument insertion port.

With such a configuration, when a treatment instrument inserted from the treatment instrument insertion port is inserted into the first hole via the forceps channel, due to a small intersection angle of the first forceps channel, the treatment instrument can be inserted into the first hole without being caught at an intersecting portion.

Further, the angle of the second forceps channel with respect to the longitudinal axis can be set to be the same intersection angle as a conventional forceps channel and hence, an opening position and an angle of the treatment instrument insertion port and a shape of an operation portion in the vicinity of the opening can be set to be the same opening position, angle, and shape as the conventional technique.

SUMMARY OF THE INVENTION

An aspect of the present invention is directed to an insertion device including: a tube having a first hole and a second hole, the first hole extending along a longitudinal axis of an insertion portion inserted into a subject, the second hole communicating with the first hole and extending in a direction intersecting with the longitudinal axis; and a frame member disposed to cover a periphery of an opening formed on an outer peripheral surface of the tube by the second hole, wherein the frame member includes a forceps channel which includes a first conduit including a first tubular path which forms a first angle, the first angle being an acute angle with respect to the longitudinal axis, and which includes an insertion port, a second conduit including a second tubular path, a first end of the second tubular path communicating with the opening, the second tubular path forming a second angle smaller than the first angle with respect to the longitudinal axis, a second end of the second tubular path being positioned on a first tubular path side, and an intermediate conduit including an intermediate tubular path which smoothly connects the first tubular path with the second tubular path, the forceps channel includes a plurality of bent regions, and curvature centers of the plurality of bent regions are disposed in different directions with respect to the forceps channel, and the first tubular path, the second tubular path, and the intermediate tubular path are seamlessly connected with each other.

DETAILED DESCRIPTION OF THE PREFERRED EMBODIMENT

Hereinafter, an embodiment of the present invention will be described with reference to drawings. In the present embodiment described hereinafter, the description will be made by taking an endoscope as an example of an insertion device.

Figure 1:
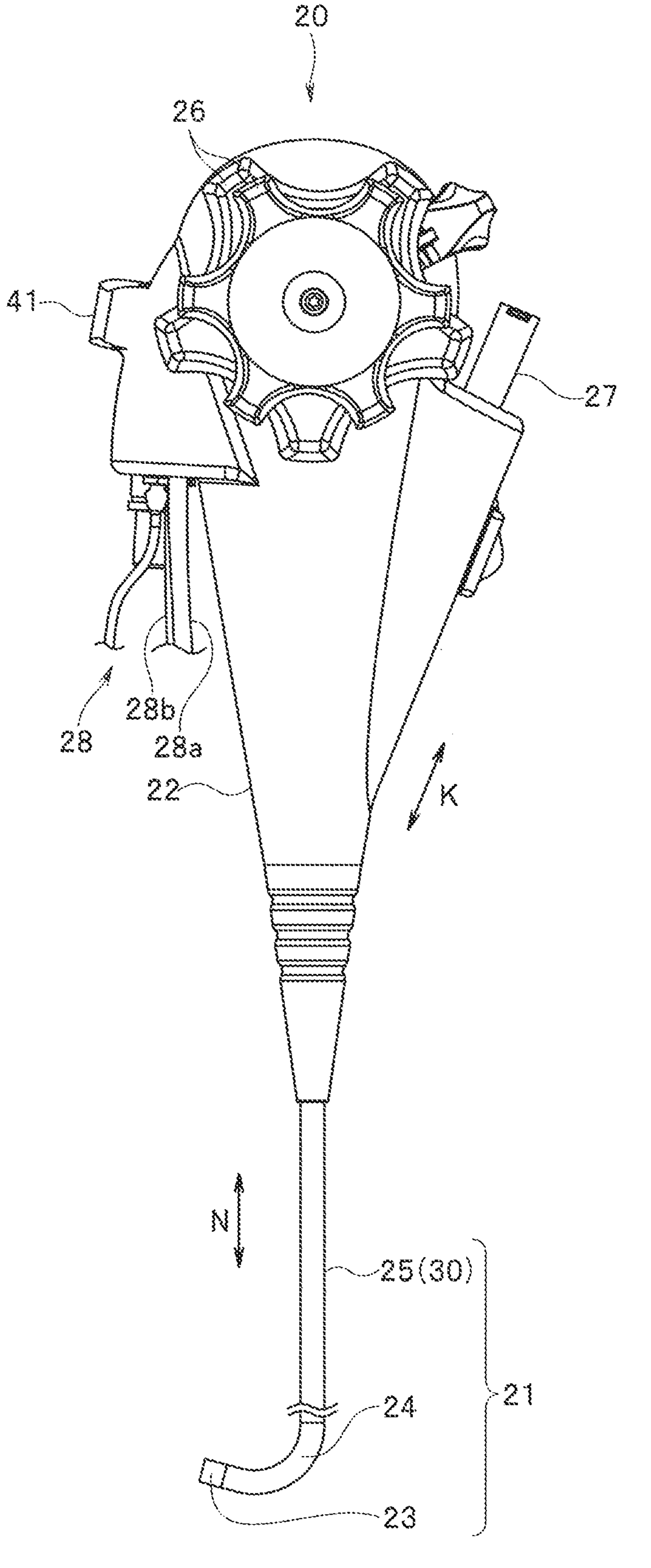
FIG. 1 is a plan view showing an endoscope of the present embodiment.

As shown in FIG. 1, an endoscope 20 includes an elongated insertion portion 21 and an operation portion 22. The insertion portion 21 is to be inserted into a subject. The operation portion 22 is continuously connected with a proximal end side of the insertion portion 21 in a direction along a longitudinal axis N (hereinafter referred to as "proximal end side").

The insertion portion 21 includes a distal end portion 23, a bending portion 24, and a flexible tube portion 25 in this order from a distal end side in the direction along the longitudinal axis N (hereinafter simply referred to as "distal end side").

The distal end portion 23 is provided with an image pickup unit and an illumination optical system (neither shown), for example. An image guide bundle is connected to the image pickup unit. The illumination optical system irradiates the subject with illumination light transmitted through a light guide bundle.

Note that in the present embodiment, the description will be made by taking a front-view type endoscope as an example of the endoscope 20, optical axes of the above-mentioned image pickup unit and illumination optical system being set along the longitudinal axis N in the front-view type endoscope.

A distal end surface of the distal end portion 23 is provided with an observation window of the image pickup unit, an illumination window of the illumination optical system, a water feeding nozzle, various openings, and the like.

With the operation of bending operation knobs 26 described later, which are provided to the operation portion 22, the bending portion 24 is bent in four directions, i.e., up, down, left, and right, for example.

In the present embodiment, the flexible tube portion 25 is formed of a tube 30 having flexibility. The tube 30 may be provided in the flexible tube portion 25.

The tube 30 is a so-called multi-lumen tube having at least one hole which extends from the distal end side to the proximal end side along the longitudinal axis N.

Figure 3:
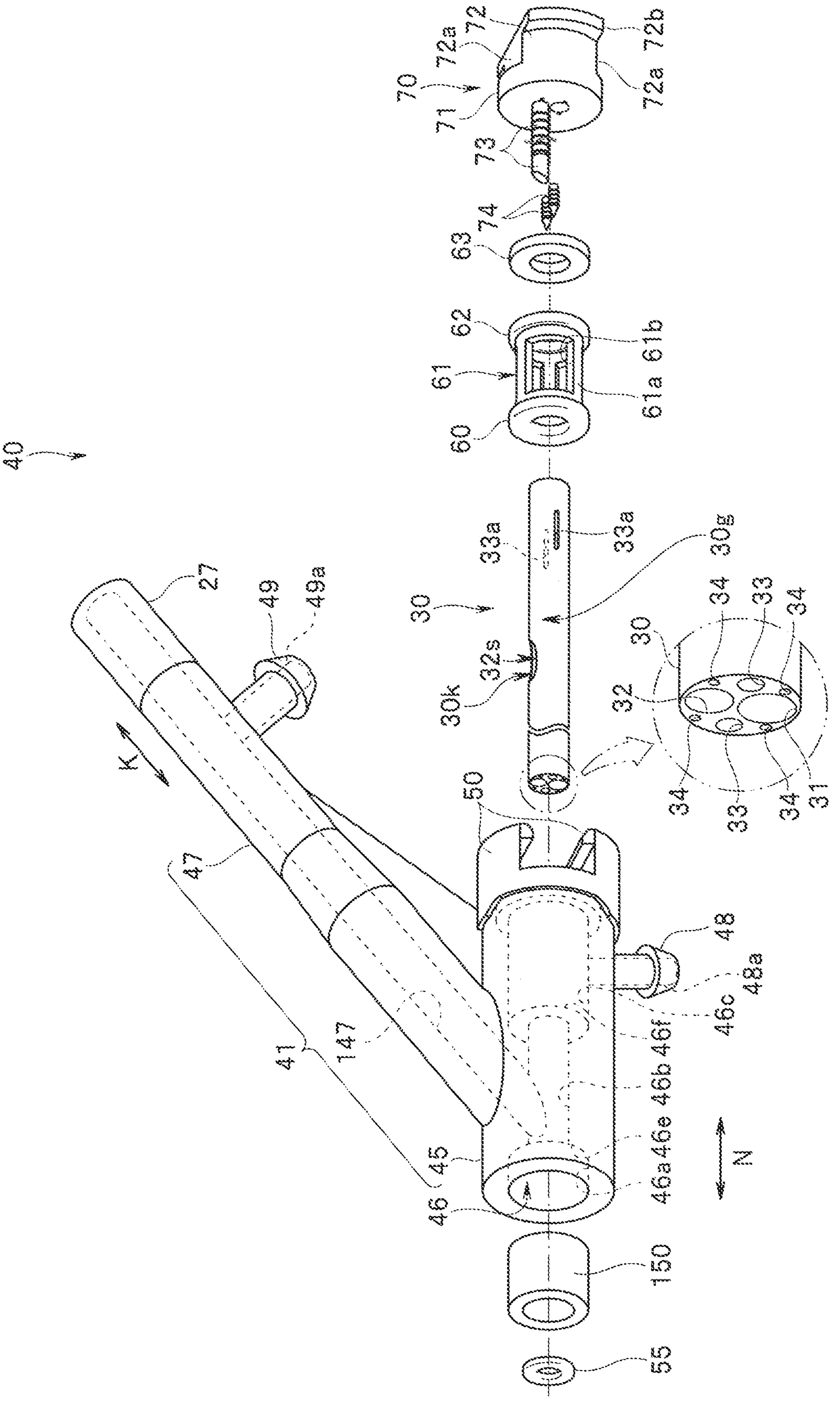
FIG. 3 is an exploded perspective view of the tube module shown in FIG. 2.
Figure 4:
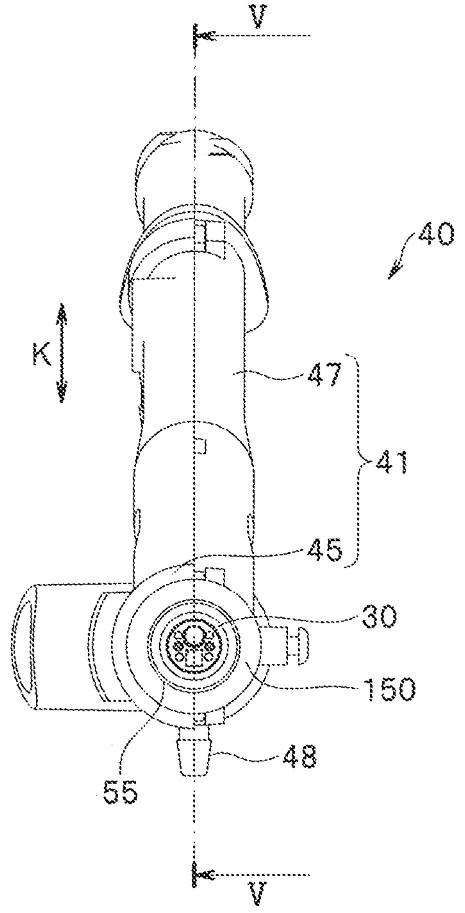
FIG. 4 is a plan view of the tube module shown in FIG. 2 as viewed in a direction IV in FIG. 2.

Specifically, as shown in FIG. 3, the tube 30 is a multi-lumen tube having eight holes, that is, an observation hole 31, a channel hole 32, a pair of water feeding holes 33, and four wire insertion holes 34. For example, the image guide bundle (or a signal line of the image pickup unit) and the light guide bundle are inserted through the observation hole 31. The channel hole 32 is an elongated first hole serving as a suction channel or a treatment instrument insertion channel. Four wires not shown in the drawing which are connected to the bending operation knobs 26 are inserted into the four wire insertion holes 34.

The number of holes of the tube 30 is not limited to eight, and the tube 30 may have any number of holes.

The flexible tube portion 25 and the bending portion 24 may be formed of the tube 30.

The operation portion 22 is provided with the pair of bending operation knobs 26 and a treatment instrument insertion pipe sleeve 27. The pair of bending operation knobs 26 is provided to perform the bending operation of the bending portion 24. The treatment instrument insertion pipe sleeve 27 is provided to insert a treatment instrument into the channel hole 32.

Cables/tubes 28 including the image guide bundle, the light guide bundle, a suction tube 28*a*, a water feeding tube 28*b*, and the like extend from the operation portion 22.

The image pickup unit may be provided to the operation portion 22. In this case, a signal cable connected to the image pickup unit extends from the operation portion 22.

On the proximal end side of the tube 30, the treatment instrument insertion pipe sleeve 27 and the suction tube 28*a* are made to communicate with the channel hole 32. Further, the water feeding tube 28*b* is made to communicate with the pair of water feeding holes 33.

Figure 2:
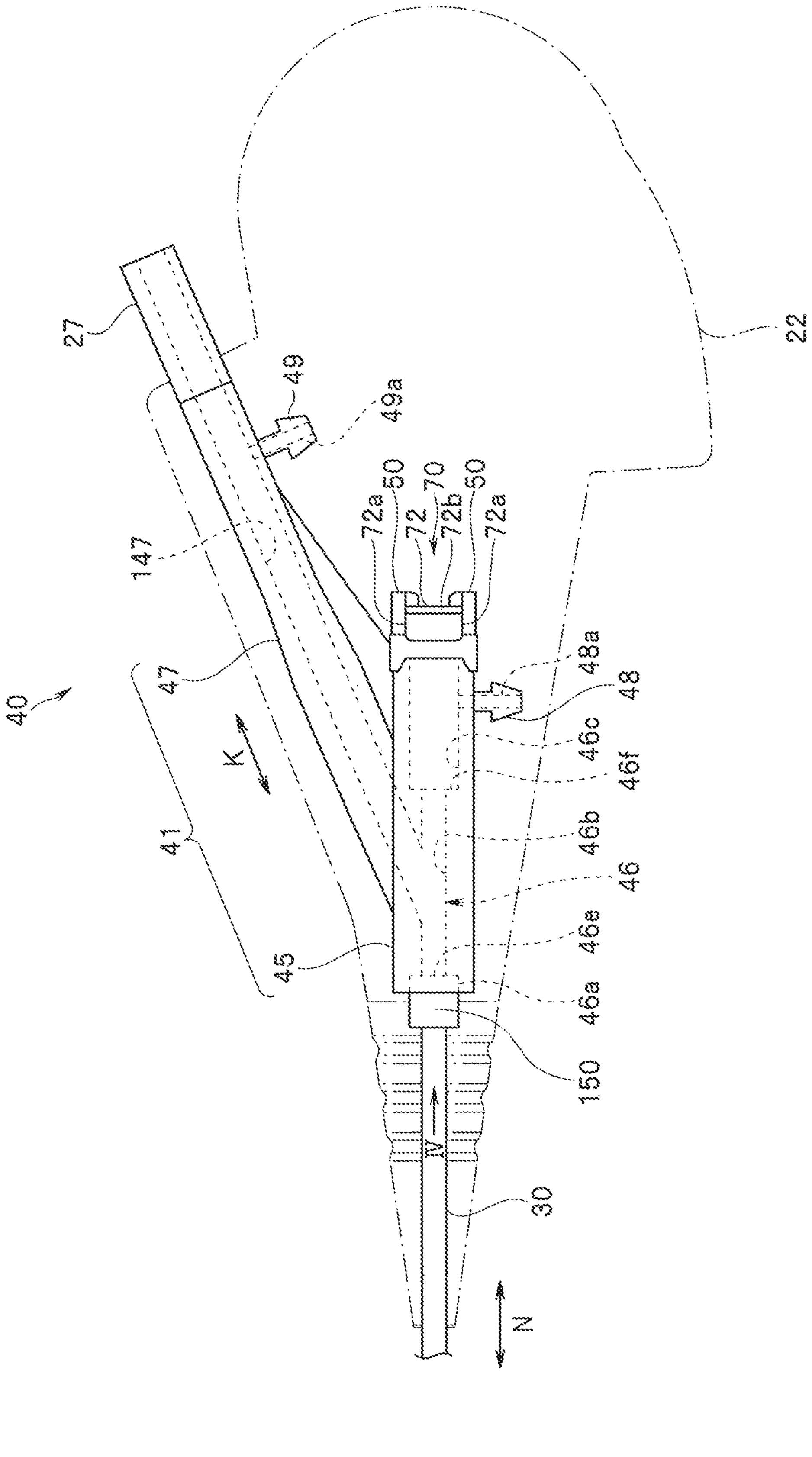
FIG. 2 is a view schematically showing a configuration of a tube module provided in an operation portion shown in FIG. 1.

To achieve the communications, in the present embodiment, a tube module 40 is provided on the proximal end side of the tube 30 as shown in FIG. 2.

As shown in FIG. 2 to FIG. 5, the tube module 40 includes a frame member 41. The frame member 41 includes a body portion 45 and a branch portion 47.

Figure 6:
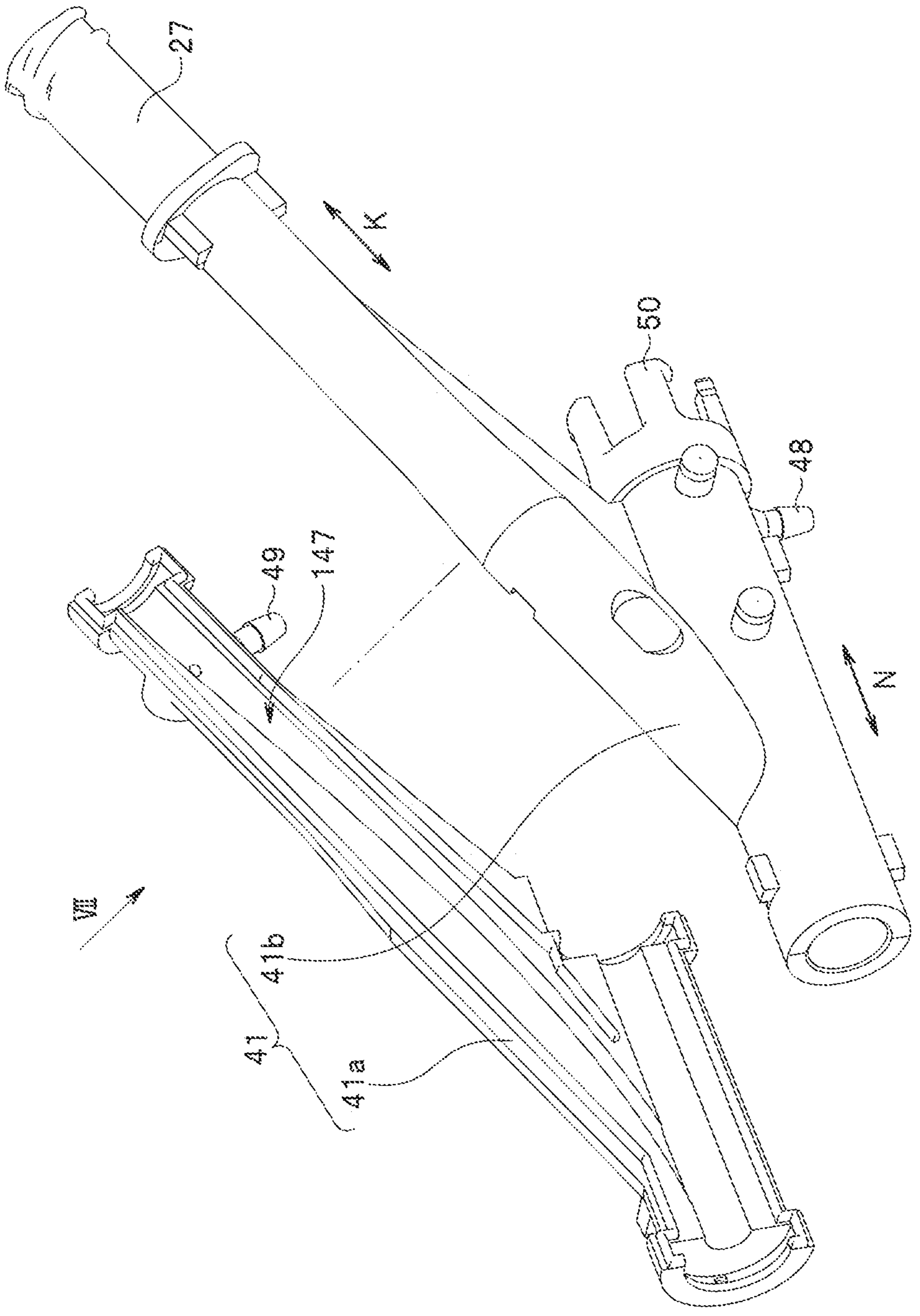
FIG. 6 is an exploded perspective view showing a modification where a frame member of the tube module shown in FIG. 2 is formed of two parts.
Figure 7:
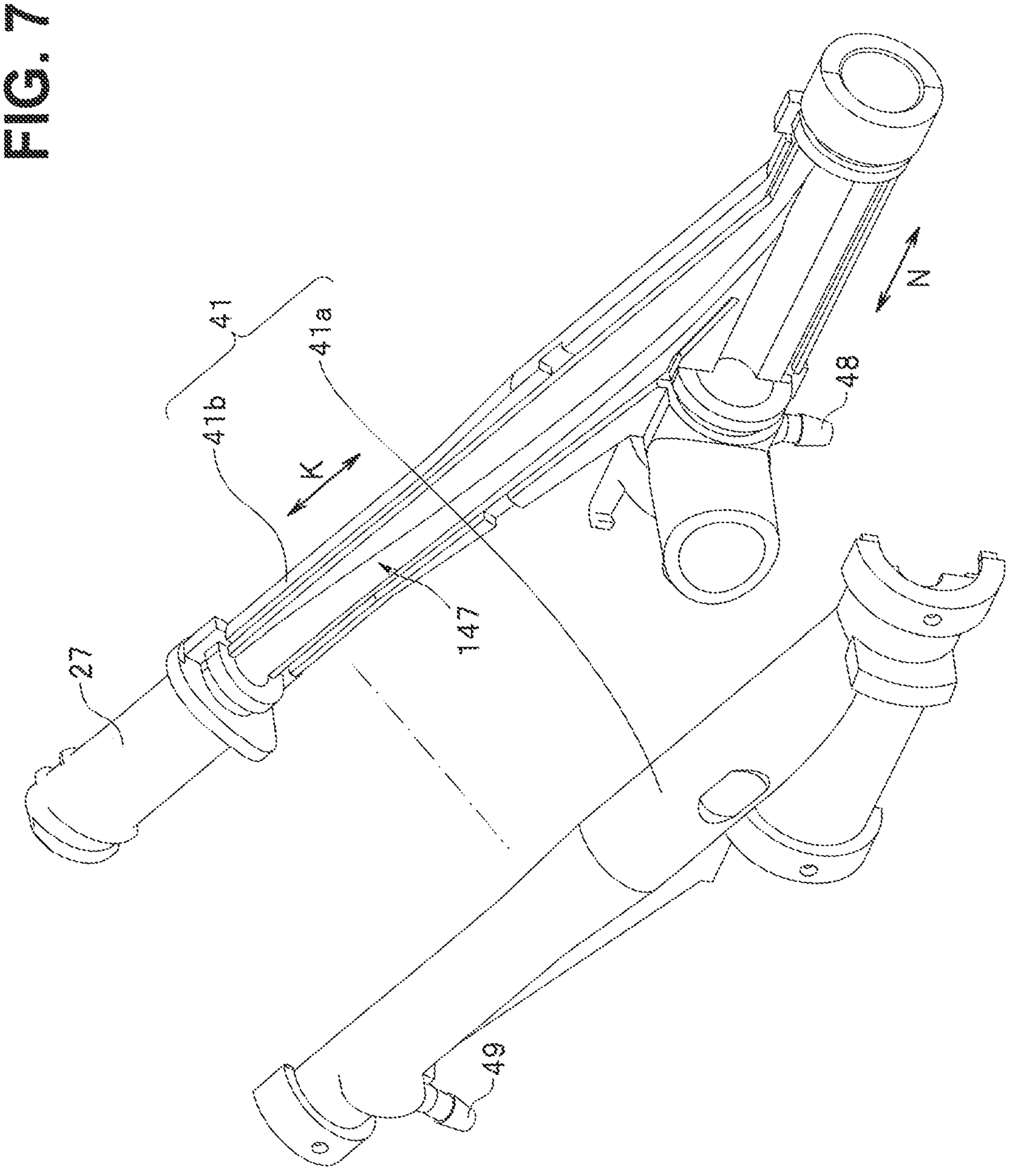
FIG. 7 is an exploded perspective view of the frame member shown in FIG. 6 as viewed in a direction VII in FIG. 6.

The entire frame member 41 may be integrally formed by a 3D printer, for example. Alternatively, as shown in FIG. 6 and FIG. 7, the frame member 41 may be formed by combining two parts 41*a*, 41*b*, each of which is formed by molding.

The frame member 41 is made of a material having high slidability, such as polycarbonate, polypropylene, polyethylene, or polyacetal. Provided that a material for forming the frame member 41 has high slidability, the material is not limited to the above-mentioned materials.

In the operation portion 22, the frame member 41 is held to cover a periphery of an opening 30*k* (see FIG. 3) which is formed on an outer peripheral surface 30*g* of the tube 30, so that the proximal end side of the tube 30 (the proximal end side of the insertion portion 21) is continuously connected to the operation portion 22.

To make the channel hole 32 and the pair of water feeding holes 33 formed in the tube 30 to communicate with the frame member 41, a second hole 32*s* and a pair of water feeding communication holes 33*a* are formed in the tube 30 on the proximal end side.

Specifically, the second hole 32*s* communicates with the channel hole 32, and is formed in the tube 30 in an intersecting direction K, which is a direction intersecting with the longitudinal axis N. An example of an angle of the intersecting direction K with respect to the longitudinal axis N may be 0° to 90°.

The tube 30 has the second hole 32*s* and hence, the outer peripheral surface 30*g* has an opening 30*k*. In other words, the second hole 32*s* is a short hole ranging from a hollow portion of the tube 30 to the opening 30*k* on the outer peripheral surface 30*g* of the tube 30.

Each water feeding communication hole 33*a* is a hole which makes the inner peripheral surface of each water feeding hole 33 to communicate with the outer peripheral surface 30*g* of the tube 30 in a direction substantially orthogonal to the longitudinal axis N.

The second hole 32*s* and the water feeding communication holes 33*a* are formed in a region close to the proximal end side of the tube 30 at positions displaced from each other in the longitudinal axis N.

Specifically, the second hole 32*s* is formed at a position displaced toward the distal end side relative to the pair of water feeding communication holes 33*a*.

Note that, in the present embodiment, the description is made by taking an example of the configuration where the pair of water feeding communication holes 33*a* is formed in the tube 30 corresponding to the pair of water feeding holes 33. However, in the case where one water feeding hole 33 is formed, it is sufficient to form the water feeding communication hole 33*a* in the tube 30 at one location.

In the case where three or more water feeding holes 33 are formed, it is sufficient to form the water feeding communication hole 33*a* in the tube 30 at three or more locations.

As shown in FIG. 3, the body portion 45 is formed to have a cylindrical shape along the longitudinal axis N, and a tube insertion hole 46 through which the tube 30 is inserted is formed in the body portion 45 along the longitudinal axis N.

The tube insertion hole 46 is formed of a stepped through hole having an inner peripheral surface with an inner diameter larger than the inner diameter of the outer peripheral surface 30*g* of the tube 30.

Specifically, the main part of the tube insertion hole 46 includes, in order from the distal end side, a first insertion hole portion 46*a*, a second insertion hole portion 46*b*, and a third insertion hole portion 46*c*, for example. The first insertion hole portion 46*a* has an inner diameter sufficiently larger than the outer diameter of the tube 30. The second insertion hole portion 46*b* has an inner diameter smaller than the inner diameter of the first insertion hole portion 46*a* (but is slightly larger than the outer diameter of the tube 30). The third insertion hole portion 46*c* has an inner diameter larger than the inner diameter of the second insertion hole portion 46*b* (for example, a diameter equal to the diameter of the first insertion hole portion 46*a*).

Further, the branch portion 47 is integrally formed with the body portion 45, the branch portion 47 extending along the intersecting direction K. The treatment instrument insertion pipe sleeve 27 is coupled with an extension end of the branch portion 47 in the intersecting direction K. A suction branch tube 49 is integrally formed with the branch portion 47 at an intermediate position in the intersecting direction K. The suction tube 28*a* is connectable to the suction branch tube 49.

A forceps channel 147 is formed in the branch portion 47 and the treatment instrument insertion pipe sleeve 27. The forceps channel 147 communicates with the second insertion hole portion 46*b* via the opening 30*k* and the second hole 32*s*.

A suction branch conduit 49*a* of the suction branch tube 49 is branched from the forceps channel 147 at an intermediate position in the intersecting direction K.

On the distal end side of the body portion 45, the first insertion hole portion 46*a* forms a portion in which a cylindrical connection pipe sleeve 150 is fitted for engagement from the distal end side.

The connection pipe sleeve 150 holds an O-shaped ring 55 which water-tightly holds the outer peripheral surface 30*g* of the tube 30 and the inner peripheral surface of the tube insertion hole 46.

The second insertion hole portion 46*b* is formed with a diameter smaller than the diameter of the first insertion hole portion 46*a*, so that a first stopper portion 46*e* is formed at a proximal end of the first insertion hole portion 46*a* in the direction along the longitudinal axis N (hereinafter referred to as "proximal end"), the first stopper portion 46*e* protruding inward from the tube insertion hole 46.

The O-shaped ring 55 is brought into contact with the first stopper portion 46*e*, so that the movement of the O-shaped ring 55 toward the proximal end side is restricted. The positioning of the O-shaped ring 55 in the connection pipe sleeve 150 is performed in this manner.

The O-shaped ring 55 is brought into close contact with the outer peripheral surface 30*g* of the tube 30 and the inner peripheral surface of the connection pipe sleeve 150 and hence, a gap formed between the tube 30 and the connection pipe sleeve 150 is air-tightly and liquid-tightly sealed by each O-shaped ring 55.

The second insertion hole portion 46*b* is provided to correspond to the second hole 32*s* which is open on the outer peripheral surface 30*g* of the tube 30.

The positioning of the tube 30 in the tube insertion hole 46 is performed such that the second hole 32*s* is positioned at the second insertion hole portion 46*b*. Therefore, the channel hole 32 formed in the tube 30 is made to communicate with the forceps channel 147 via the second hole 32*s* and the opening 30*k*.

The third insertion hole portion 46*c* is provided to correspond to the water feeding communication holes 33*a* which are open on the outer peripheral surface 30*g* of the tube 30.

Figure 5:
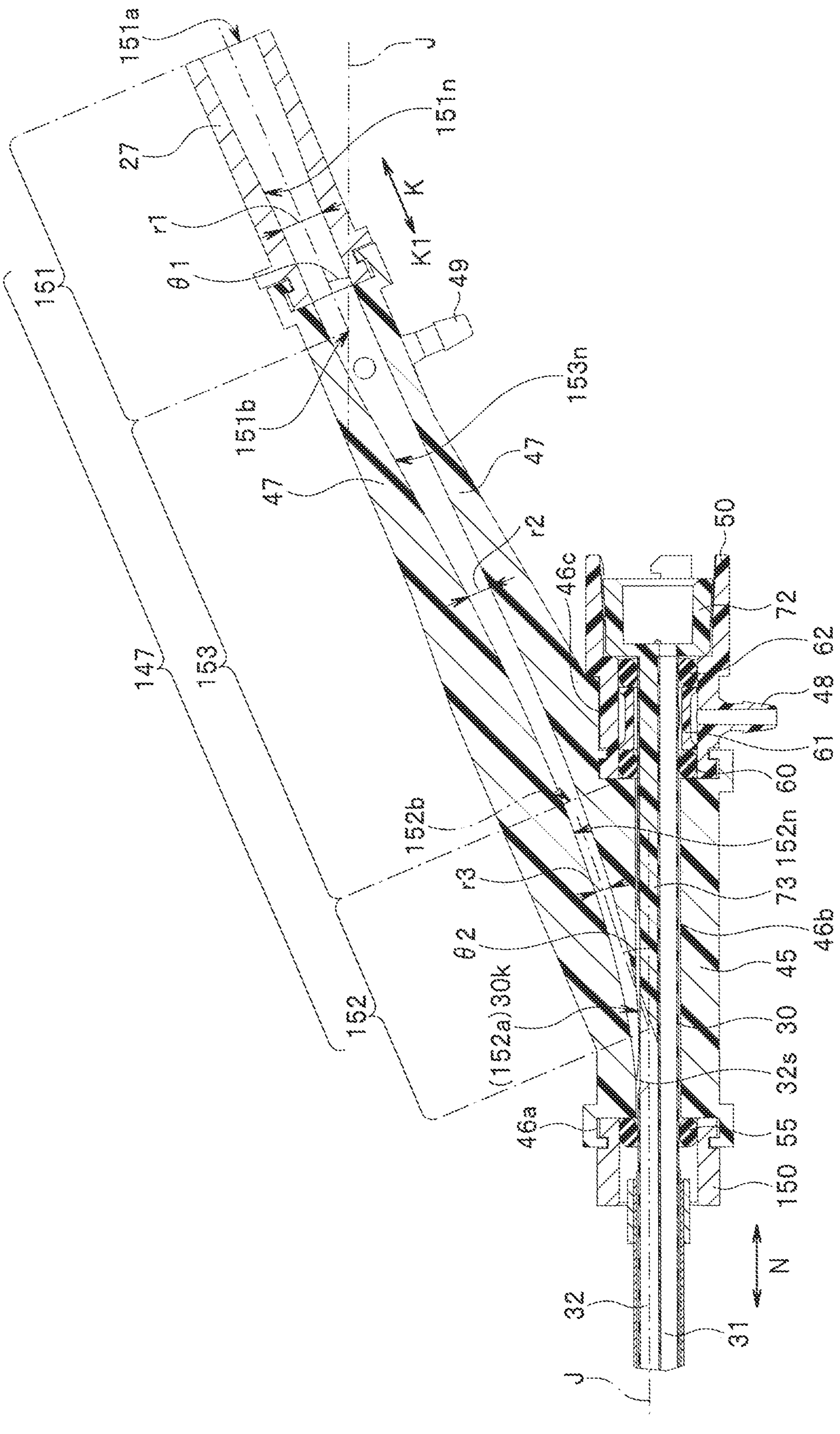
FIG. 5 is a cross-sectional view of the tube module taken along line V-V.

As shown in FIG. 5, a pair of locking claw portions 50 is inserted into the third insertion hole portion 46*c*. A water feeding branch tube 48 is integrally formed with the pair of claw portions 50.

A water feeding branch conduit 48*a* communicating with the third insertion hole portion 46*c* is formed in the water feeding branch tube 48. The water feeding tube 28*b* is connectable to the water feeding branch tube 48.

An O-shaped ring 60, a cylindrical spacer 61, an O-shaped ring 62, and an annular adjusting ring 63 are inserted into the pair of locking claw portions 50 in this order from the proximal end side of the body portion 45.

The second insertion hole portion 46*b* is formed with a diameter smaller than the diameter of the third insertion hole portion 46*c*, so that a second stopper portion 46*f* is formed at a distal end of the third insertion hole portion 46*c*, the second stopper portion 46*f* protruding inward from the tube insertion hole 46.

The O-shaped ring 60 and the pair of claw portions 50 are brought into contact with the second stopper portion 46*f*, so that the movement of the O-shaped ring 60 and the pair of claw portions 50 toward the distal end side is restricted. The positioning of the pair of claw portions 50, the O-shaped ring 60, the spacer 61, the O-shaped ring 62, and the adjusting ring 63 in the third insertion hole portion 46*c* is performed in this manner.

Specifically, the O-shaped ring 60 is brought into contact with the second stopper portion 46*f*, thus being positioned at a position closer to the distal end side than the water feeding communication holes 33*a* and the water feeding branch conduit 48*a* in the third insertion hole portion 46*c*.

The O-shaped ring 60 which is positioned as described above is brought into close contact with the outer peripheral surface 30*g* of the tube 30 and the inner peripheral surfaces of the pair of claw portions 50. Therefore, at a position closer to the distal end side than the water feeding communication holes 33*a* and the water feeding branch conduit 48*a*, a gap formed between the outer peripheral surface 30*g* of the tube 30 and the pair of claw portions 50 is air-tightly and liquid-tightly sealed by the O-shaped ring 60.

The spacer 61 is brought into contact with the O-shaped ring 60, thus being positioned at a position which corresponds to the water feeding communication holes 33*a* and an opening portion of the water feeding branch conduit 48*a* in the third insertion hole portion 46*c*.

The spacer 61 includes wall portions 61*a* forming a substantially cylindrical shape, the wall portions 61*a* being disposed between the tube 30 and the third insertion hole portion 46*c* (the tube insertion hole 46) at predetermined intervals.

Communication holes 61*b*, which make the inner surface side and the outer surface side of the wall portions 61*a* communicate with each other, are each formed between the wall portions 61*a* of the spacer 61.

The spacer 61 having such communication holes 61*b* is disposed at a position which corresponds to the water feeding communication holes 33*a* and the opening portion of the water feeding branch conduit 48*a* and hence, each of the pair of water feeding holes 33 formed in the tube 30 is made to communicate with the water feeding branch conduit 48*a*.

The O-shaped ring 62 is brought into contact with the spacer 61, thus being positioned within the pair of claw portions 50 at a position closer to the proximal end side than the water feeding communication holes 33*a* and the water feeding branch conduit 48*a*.

The O-shaped ring 62 which is positioned as described above is brought into close contact with the outer peripheral surface 30*g* of the tube 30 and the inner peripheral surfaces of the pair of claw portions 50. Therefore, at a position closer to the proximal end side than the water feeding communication holes 33*a* and the water feeding branch conduit 48*a*, a gap formed between the outer peripheral surface 30*g* of the tube 30 and the pair of claw portions 50 is air-tightly and liquid-tightly sealed by the O-shaped ring 62. Note that the O-shaped ring 60, the spacer 61, and the O-shaped ring 62 are integrally formed in advance.

The adjusting ring 63 is brought into contact with the O-shaped ring 62, thus being positioned at the proximal end side within the pair of claw portions 50.

An end part member 70 is held in the pair of claw portions 50, the end part member 70 being provided for closing the proximal ends of the pair of claw portions 50.

The main part of the end part member 70 is formed such that a lid body 71 and a cylindrical portion 72 are integrally formed with each other. The lid body 71 is provided to close the pair of claw portions 50. The cylindrical portion 72 extends toward the proximal end side of the lid body 71.

A pin-shaped sealing member 73 is provided to the distal end surface of the lid body 71 in a protruding manner at a position which corresponds to the channel hole 32. The sealing member 73 is made of polycarbonate, polypropylene, polyethylene, or polyacetal, for example.

As shown in FIG. 5, the sealing member 73 is inserted into the channel hole 32, thus sealing the proximal end side of the channel hole 32, and causing the proximal end side of the tube 30 to couple with the end part member 70.

When the tube 30 is caused to couple with the end part member 70, pin-shaped sealing members 74 of the end part member 70 are respectively inserted into proximal end portions of the water feeding holes 33. With such a configuration, the proximal end side of each water feeding hole 33 is sealed by the sealing member 74.

Through holes not shown in the drawing are formed in the lid body 71 at positions which correspond to the observation hole 31 and the respective wire insertion holes 34, the through holes penetrating the lid body 71 along the longitudinal axis N. The end part member 70 is coupled to the proximal end side of the tube 30 by using the sealing members 74, so that the observation hole 31 and the respective wire insertion holes 34 are made to communicate with the inner portion (inside) of the cylindrical portion 72 via the respective through holes.

The observation hole 31 and the respective wire insertion holes 34 are made to communicate with the inner portion of the cylindrical portion 72 via the respective through holes as described above and hence, it is possible to insert the image guide bundle and the light guide bundle into the observation hole 31 from the inner portion of the cylindrical portion 72, and it is also possible to allow insertion of the wire into each wire insertion hole 34.

The outer peripheral surface of the cylindrical portion 72 has a pair of cutout portions 72*a*. A flange portion 72*b* is provided to a proximal end portion of the cylindrical portion 72 excluding regions of the cutout portions 72*a*, the flange portion 72*b* protruding in an outer diameter direction.

The proximal end of the cylindrical portion 72 is locked to the pair of locking claw portions 50, so that the lid body 71 of the end part member 70 is held within the pair of locking claw portions 50.

In such a state, the tube 30 is pushed by the end part member 70 within the pair of locking claw portions 50, so that positioning of the proximal end position of the tube 30 with respect to the body portion 45 is automatically performed along the longitudinal axis N.

With such an operation, the positioning of the tube 30 along the longitudinal axis N within the pair of locking claw portions 50 is automatically performed. Therefore, the second hole 32*s* is disposed in the second insertion hole portion 46*b*, and the water feeding communication holes 33*a* are disposed in the third insertion hole portion 46*c*.

Further, the cutout portions 72*a* and the flange portion 72*b* are sandwiched between the pair of locking claw portions 50, so that positioning of a rotational position of the end part member 70 about the longitudinal axis N is performed.

With the positioning of the rotational position of the end part member 70, positioning of the rotational position of the tube 30 about the longitudinal axis N in the tube insertion hole 46 is automatically performed. Therefore, the second hole 32*s* is disposed in the second insertion hole portion 46*b* at a position which matches with the forceps channel 147.

The O-shaped ring 60, the spacer 61, and the O-shaped ring 62 are sandwiched between the second stopper portion 46*f* and the end part member 70 by using the adjusting ring 63, so that the O-shaped ring 60, the spacer 61, and the O-shaped ring 62 are held in a state of being positioned at predetermined positions which use the second stopper portion 46*f* as the reference.

Next, a configuration of the branch portion 47 will be described with reference to FIG. 5 to FIG. 7.

As shown in FIG. 5, the branch portion 47 is formed to extend in the intersecting direction K. The branch portion 47 includes a first conduit 151, a second conduit 152, and an intermediate conduit 153, the first conduit 151 including the treatment instrument insertion pipe sleeve 27. Further, as described above, the forceps channel 147 is formed in the branch portion 47 and the treatment instrument insertion pipe sleeve 27.

Specifically, a first tubular path, which is an elongated hollow portion of the first conduit 151, is formed in the branch portion 47 and the treatment instrument insertion pipe sleeve 27. The first tubular path forms a first angle $\theta 1$, which is an acute angle with respect to an axis J, which is parallel to the longitudinal axis N. The first tubular path has an insertion port 151*a* for a treatment instrument, the insertion port 151*a* being open to a space outside the frame member 41.

A second tubular path, which is an elongated hollow portion of the second conduit 152, is formed in the branch portion 47. A first end 152*a* communicates with the opening 30*k*, and a second end 152*b* is positioned on the first conduit 151 side in the intersecting direction K.

The second tubular path is formed with a second angle θ2 smaller than the first angle θ1 (θ2<θ1) with respect to the axis J.

The second tubular path includes a bent region, at least a portion of which is bent. Note that the entire second tubular path may have a linear shape.

The second angle θ2 is set to be larger than 0° and smaller than 60°. More specifically, it is desirable that the second angle θ2 be set to be 10° or more and less than 20°.

It is preferable that the first angle θ1 be an angle which is larger than θ2 and smaller than 90°. It is desirable that the first angle θ1 be an angle which is larger than 30° and smaller than 50°.

An intermediate tubular path, which is an elongated hollow portion of the intermediate conduit 153, connects the first tubular path with the second tubular path in the intersecting direction K, the first tubular path and the second tubular path having different angles with respect to the axis J. The intermediate tubular path smoothly connects an end portion 151*b* of the first tubular path and the second end 152*b* of the second tubular path, the end portion 151*b* being disposed on an opposite side of the insertion port 151*a* in the intersecting direction K.

Figure 8:
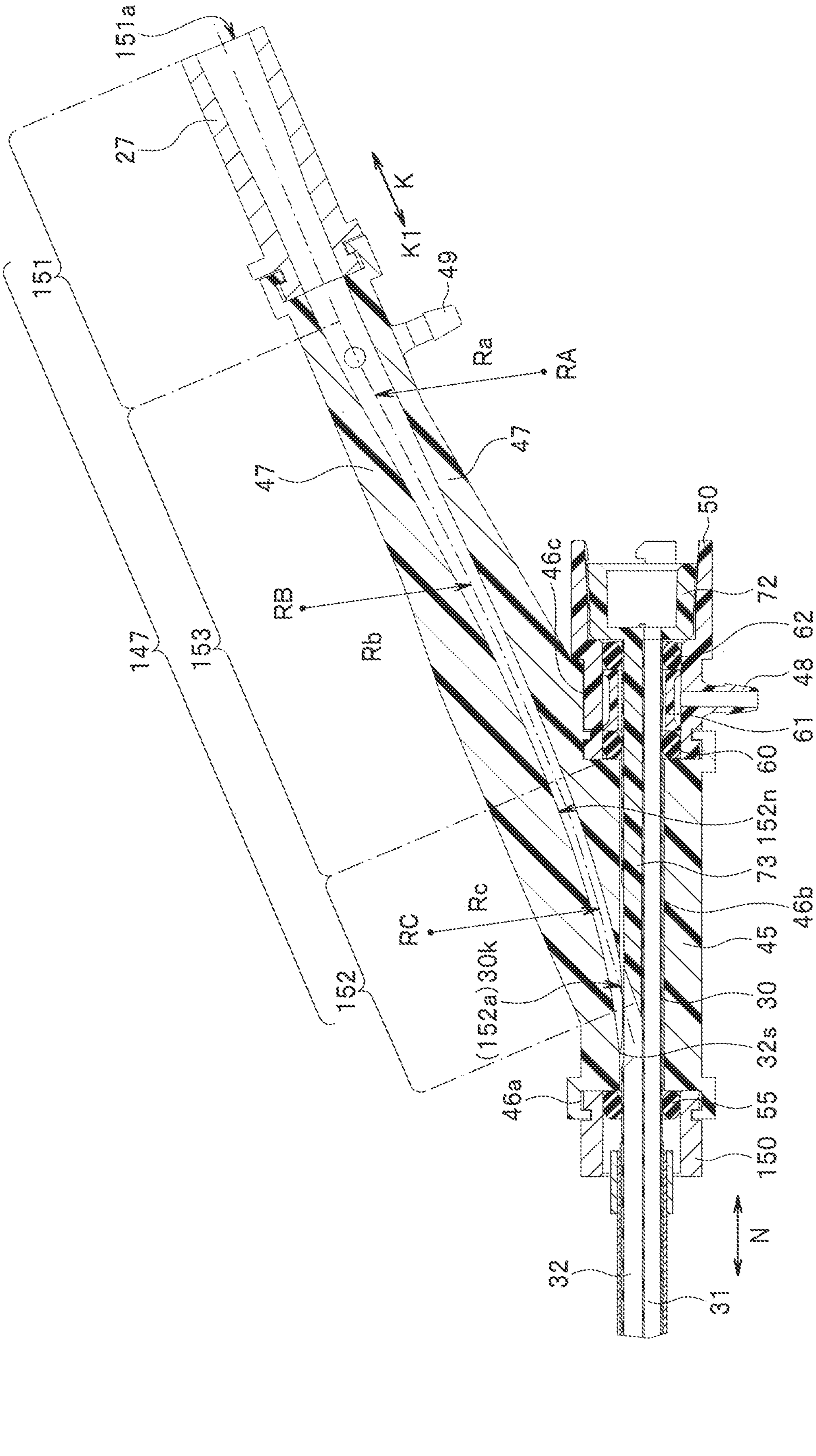
FIG. 8 is a view showing a curvature radius of an intermediate portion of a forceps channel in cross section of the tube module shown in FIG. 5.

The forceps channel 147 includes at least two or more bent regions. Specifically, as shown in FIG. 8, in the present embodiment, the forceps channel 147 includes three bent regions with curvature radii Ra, Rb, Rc. As shown in FIG. 8, a curvature center RA of the bent region with the curvature radius Ra is disposed in a direction different from a direction of curvature centers RB, RC of the bent regions with curvature radii Rb, Rc with respect to the forceps channel 147. In other words, the curvature centers RB, RC of the bent regions with the curvature radii Rb, Rc are disposed frontward of the forceps channel 147 (in a first direction, which is a direction in which the second hole 32*s* is provided to the channel hole 32 being the first hole). In contrast, the curvature center RA of the bent region with the curvature radius Ra is disposed rearward of the forceps channel 147 (in a second direction). In other words, the curvature center RA is disposed at a position opposite to positions of the curvature centers RB, RC, the position of the curvature center RA being disposed in a direction different from a direction of the curvature centers RB, RC with respect to the forceps channel 147. The plurality of curvature centers RA, RB, RC include two kinds of curvature centers which are disposed at positions opposite to each other (in the forward direction and a rearward direction) with respect to the forceps channel 147.

Therefore, insertion of a treatment instrument from the insertion port 151*a* to the bent region with the curvature radius Ra can be especially easily performed.

Note that the intermediate conduit 153 includes the bent region with the curvature radius Ra and the bent region with the curvature radius Rb, and the second conduit 152 includes the bent region with the curvature radius Rc.

An inner diameter r2 of the second tubular path is formed to be smaller than an inner diameter r1 of the first tubular path, and an inner diameter r3 of the intermediate tubular path is formed to be smaller than the inner diameter r1, but larger than the inner diameter r2 (r1>r3>r2).

In other words, the inner diameter of the forceps channel 147 is formed to reduce in a stepwise manner from the insertion port 151*a* toward the first end 152*a*.

In the forceps channel 147 having such a configuration, an inner peripheral surface 151*n* of the first tubular path and an inner peripheral surface 152*n* of the second tubular path are seamlessly connected by the intermediate tubular path.

As described above, the forceps channel 147 may be formed in the branch portion 47 by integrally forming the entire frame member 41 by a 3D printer, for example. Alternatively, as shown in FIG. 6 and FIG. 7, the forceps channel 147 may be formed in the branch portion 47 by combining the two parts 41*a*, 41*b*, each of which is formed by molding.

However, the method of forming the forceps channel 147 by combining the two parts 41*a*, 41*b* as shown in FIG. 6 and FIG. 7 can more easily achieve the forceps channel 147, including the bent regions with predetermined curvature radii, with high accuracy.

In both the case where the frame member 41 is integrally formed and the case where the frame member 41 is formed by combining the two parts 41*a*, 41*b*, the forceps channel 147, which includes the first tubular path, the second tubular path, and the intermediate tubular path, is formed seamlessly in the intersecting direction K as shown in FIG. 5.

In the case where the frame member 41 is formed of the two parts 41*a*, 41*b*, a joint portion between the two parts 41*a*, 41*b* is formed in a direction about the intersecting direction K. However, also in this case, each of the parts 41*a*, 41*b* has a seamless shape in the intersecting direction K as shown in FIG. 6 and FIG. 7 and hence, the forceps channel 147 can be formed seamlessly in the intersecting direction K.

As described above, the frame member 41 is made of a material having high slidability, such as polycarbonate, polypropylene, polyethylene, or polyacetal. Such a configuration is adopted to increase slidability of a treatment instrument with respect to the forceps channel 147.

Even if the frame member 41 is made of a material having low slidability, it is possible to increase slidability of a treatment instrument with respect to the forceps channel 147 by applying fluorine based coating or the like to the forceps channel 147.

A treatment instrument is inserted into the forceps channel 147 having such a configuration via the insertion port 151*a*.

The treatment instrument inserted from the insertion port 151*a* passes through the first tubular path, the intermediate tubular path, and the second tubular path, and is then inserted into the second hole 32*s* and the channel hole 32 from the opening 30*k*, with which the first end 152*a* communicates. Thereafter, the treatment instrument is caused to protrude from a protrusion port of the channel hole 32, the protrusion port being formed in a distal end surface of the distal end portion 23.

Other components of the endoscope 20 are well-known and hence, the description of such components will be omitted.

As described above, in the present embodiment, the forceps channel 147 is formed in the branch portion 47 and the treatment instrument insertion pipe sleeve 27 to extend in the intersecting direction K, and the main part of the forceps channel 147 includes the first conduit 151, the second conduit 152, and the intermediate conduit 153.

In the forceps channel 147, from the insertion port 151*a* to the first end 152*a* in the intersecting direction K, the inner peripheral surface 151*n* of the first tubular path and the inner peripheral surface 152*n* of the second tubular path are seamlessly connected by the intermediate tubular path at least in a direction K1 from the insertion port 151*a* toward the first end 152*a*.

With such a configuration, a treatment instrument inserted into the forceps channel 147 can be caused to smoothly pass through from the insertion port 151*a* to the first end 152*a* with low insertion resistance and without being caught.

In the above-mentioned present embodiment, the first tubular path is formed with the first angle θ1, which is an acute angle with respect to the axis J, and the second tubular path is formed with the second angle θ2 smaller than the first angle θ1 (θ2<θ1) with respect to the axis J.

The intermediate tubular path connects the first tubular path with the second tubular path having different angles with respect to the axis J, and includes the two bent regions with curvature radii Ra, Rb.

With such a configuration, the second angle θ2 of the second tubular path, which has the first end 152*a* communicating with the opening 30*k* of the tube 30, can be set to be smaller than an angle of a forceps channel of a conventional endoscope. Therefore, a treatment instrument in the forceps channel 147 can be smoothly and quickly inserted into the channel hole 32 via the opening 30*k* and the second hole 32*s*.

Note that the reason is as follows. As described above, at least a portion of the second tubular path is formed into a bent shape and hence, the treatment instrument in the forceps channel 147 can be more smoothly and quickly inserted into the channel hole 32 via the opening 30*k* and the second hole 32*s*.

Even if the second angle θ2 of the second tubular path is set to be smaller than a corresponding angle of the conventional endoscope, the intermediate tubular path including the bent regions allows smooth connection with the first tubular path having the first angle θ1, which is larger than the second angle θ2, without the treatment instrument being caught in the intersecting direction K. In other words, since the intermediate tubular path includes the bent regions, the second angle θ2 of the second tubular path can be set to be smaller than the corresponding angle of the conventional endoscope.

When the first angle θ1 is set to the same angle as that of the conventional endoscope, it is sufficient to merely change the conventional shape of the forceps channel 147, and the position and the angle of the insertion port 151*a* can be set to the same position and angle in the operation portion 22 as the conventional endoscope.

Therefore, the shape of the operation portion 22, that is, the outer shape of the frame member 41 can be maintained to be the same shape as the conventional endoscope and hence, the outer shape of the frame member can be maintained to be a shape which is optimum for the insertion of a treatment instrument. Accordingly, it is possible to maintain ease of insertion of the treatment instrument into the insertion port 151*a*.

Further, the intermediate tubular path includes at least two or more bent regions. In the present embodiment, the intermediate tubular path includes two bent regions with curvature radii Ra, Rb.

With such a configuration, a treatment instrument can be caused to smoothly pass through from the first tubular path to the second tubular path without the treatment instrument being caught in the intermediate tubular path.

In the present embodiment, the inner diameter r2 of the second tubular path is formed to be smaller than the inner diameter r1 of the first tubular path, and the inner diameter r3 of the intermediate tubular path is formed to be smaller than the inner diameter r1, but larger than the inner diameter r2. (r1>r3>r2)

The inner diameter of the forceps channel 147 is formed to reduce in a stepwise manner from the insertion port 151*a* toward the first end 152*a*.

With such a configuration, even when a treatment instrument with a rigid distal portion having a large length is inserted into the forceps channel 147, there is no possibility of the treatment instrument being caught in the intermediate tubular path including the bent regions.

Accordingly, it is possible to provide the endoscope 20, where a treatment instrument can be quickly inserted into the channel hole 32 of the tube 30 without being caught, without changing the shape of the operation portion 22 at a portion which corresponds to the opening of the insertion port 151*a*, or the opening position and the angle of the insertion port 151*a*.

Note that in the above-mentioned present embodiment, the endoscope 20 has been described as an example of the insertion device. However, the insertion device is not limited to the above. Needless to say, the insertion device may be another insertion device including the tube 30 for the insertion of a treatment instrument. The applications for the endoscope may be either medical applications or industrial applications.

The present invention is not limited to the above-mentioned embodiment and the like, and various modifications, combinations, and applications are conceivable without departing from the gist of the invention.

What is claimed is:

1. An insertion device comprising:
- a tube comprising an opening disposed on a circumferential surface of the tube, the tube extending along a longitudinal axis; and
- a frame comprising:
  - a first conduit comprising an insertion port, an axis of the first conduit having a first angle relative to the longitudinal axis, and
  - a second conduit comprising an end connected to the opening, the second conduit being in fluid communication with the first conduit, the end having a second angle relative to the longitudinal axis, the second angle being smaller than the first angle, the second conduit comprising a plurality of curved portions connected seamlessly to each other, each of the plurality of curved portions having a different finite radius of curvature.

2. The insertion device according to claim 1, wherein the plurality of curved portions comprises:
- a first curved portion having a first curvature center, the first curvature center disposed on a first side relative to a center axis of the second conduit; and
- a second curved portion having a second curvature center, the second curvature center disposed on a second side relative to the center axis of the second conduit, the second side being opposite to the first side across the center axis of the second conduit.

3. The insertion device according to claim 1, wherein a second inner diameter of the second conduit is smaller than a first inner diameter of the first conduit.

4. The insertion device according to claim 1, wherein the frame is formed of a plurality of parts, and the plurality of parts together form the first conduit and the second conduit.

5. The insertion device according to claim 1, wherein the tube is a multi-lumen tube having a plurality of channels.

6. The insertion device according to claim 5, wherein the opening is in fluid communication with a channel of the plurality of channels.

7. The insertion device according to claim 1, wherein the second conduit comprises:

a first portion; and a second portion disposed between the first conduit and the first portion.

8. The insertion device according to claim 7, wherein a second inner diameter of the second portion is smaller than a first inner diameter of the first conduit; and the second inner diameter of the second portion is larger than a third inner diameter of the first portion.

9. The insertion device according to claim 1, wherein the first angle is an acute angle.

10. The insertion device according to claim 1, wherein the frame comprises:

a body portion extending along the longitudinal axis, the tube is disposed in the body portion; and a branch portion extending in a direction intersecting with the longitudinal axis, the branch portion comprising the first conduit and the second conduit.

11. The insertion device according to claim 1, wherein the insertion port is open to an outside of the frame.

12. The insertion device according to claim 7, wherein the second portion includes at least two of the plurality of curved portions.

13. The insertion device according to claim 4, wherein each of the plurality of parts has a seamless shape in a direction intersecting with the longitudinal axis.

14. An endoscope comprising:

an insertion portion;

an operation portion provided proximally relative to the insertion portion; and the insertion device according to claim 1 disposed in the operation portion, wherein at least a portion of the tube is disposed in the insertion portion, the insertion port is configured to receive a forceps, and the first conduit comprises a treatment instrument insertion pipe sleeve.

15. An insertion device comprising:

a frame comprising:

a body portion extending along a longitudinal axis; and a branch portion extending in a direction intersecting with the longitudinal axis, the branch portion comprising:

a first conduit comprising an insertion port, an axis of the first conduit having a first angle relative to the longitudinal axis; and a second conduit comprising a first end in communication with an opening in the body portion, the first end having a second angle relative to the longitudinal axis, the second angle being smaller than the first angle, the second conduit comprising a plurality of curved portions;

wherein each of the plurality of curved portions has a finite curvature radius greater than zero and each of the plurality of curved portions having a different radius of curvature.

16. The insertion device according to claim 15, wherein the plurality of curved portions comprises:

a first curved portion having a first curvature center, the first curved portion being closest to the first conduit, the first curvature center disposed on a first side relative to a center axis of the second conduit; and a second curved portion having a second curvature center, the second curvature center disposed on a second side relative to the center axis of the second conduit, the second side being opposite to the first side across the center axis of the second conduit.

17. The insertion device according to claim 1, wherein the second conduit is seamlessly connected to the first conduit.

18. The insertion device according to claim 2, wherein the first curved portion is closest to the first conduit.

19. The insertion device according to claim 1, wherein the plurality of curved portions are connected seamlessly to each other in a center axis direction of the second conduit.

20. The insertion device according to claim 15, wherein the plurality of curved portions are connected seamlessly to each other in a center axis direction of the second conduit.

21. The insertion device according to claim 1, wherein the opening is disposed between a first end and a second end of the tube.

22. The insertion device according to claim 2, wherein the frame includes a first wall portion being on the first side and a second wall portion being on the second side, the second wall portion is thicker than the first wall portion around the second curved portion.

* * * * *